(12) United States Patent
Benz et al.

US007741375B2

(10) Patent No.: US 7,741,375 B2
(45) Date of Patent: Jun. 22, 2010

(54) POLYKETAL POLYMERS, AND METHODS OF MAKING AND USING SAME

(75) Inventors: Michael Eric Benz, Ramsey, MN (US); Lian Leon Luo, Shoreview, MN (US)

(73) Assignee: Medtronic, Inc, Minneapolis, MN (US)

( * ) Notice: Subject to any disclaimer, the term of this patent is extended or adjusted under 35 U.S.C. 154(b) by 543 days.

(21) Appl. No.: 11/706,508

(22) Filed: Feb. 15, 2007

(65) Prior Publication Data
US 2007/0265355 A1    Nov. 15, 2007

Related U.S. Application Data

(60) Provisional application No. 60/774,908, filed on Feb. 17, 2006.

(51) Int. Cl.
*A61K 47/30* (2006.01)
*C07D 303/12* (2006.01)
*C07C 41/00* (2006.01)

(52) U.S. Cl. .................. 514/772; 549/554; 568/579; 568/626; 568/671

(58) Field of Classification Search .................. None
See application file for complete search history.

(56) References Cited

U.S. PATENT DOCUMENTS

| 3,475,461 | A | 10/1969 | Lloyd |
| 4,374,953 | A | 2/1983 | Chou et al. |
| 4,774,344 | A | 9/1988 | Kelsey |
| 4,898,928 | A | 2/1990 | Heller et al. |
| 5,863,990 | A | 1/1999 | Papisov |
| 6,133,402 | A | 10/2000 | Coates et al. |
| 6,730,772 | B2 * | 5/2004 | Shastri .................. 528/354 |

FOREIGN PATENT DOCUMENTS

| EP | 0105487 A1 | 4/1984 |
| EP | 0105487 B1 | 1/1991 |
| EP | 1468036 A2 | 7/2003 |
| EP | 1534269 A1 | 1/2004 |
| GB | 1041084 | 9/1966 |
| GB | 1123907 | 8/1968 |
| GB | 1369386 | 10/1974 |
| JP | 2004-256804 | 9/2004 |
| WO | WO 03/000766 A1 | 1/2003 |
| WO | WO 2005/023294 A2 | 3/2005 |
| WO | WO 2005/023294 A3 | 6/2005 |

OTHER PUBLICATIONS

Mitchell, Philip, Tool and Manufacturing Engineers handbook: Plastic part manufacturing, Edition 4, V 8, 1996 pp. 1-2.*
Curci, Ruggero et. al., Epoxidation of Alkenes by Dioxirane Intermediates Generated in the Reaction of Potassium Caroate with Ketones, J. Org. Chem. 1980, 45, pp. 4758-4760.*
Broshears et al., "Simple Epoxide Formation for the Organic Laboratory Using Oxone" *J. Chem. Educ.*, Jul. 2004; 81(7):1018-1019.
Johnson et al., "The total synthesis of cycloheximide" *J. Am. Chem. Soc.*, Jan. 1966: 88:149-159.
Levene et al., "Studies in polymerization and condensation. VI. 5,6-dihydroxyhexanone-2." *J. Biol. Chem.*, 1930; 88(3):771-790.
Moore et al., "Mechanism of the alternating copolymerization of epoxides and $CO_2$ using beta-diiminate zinc catalysts: evidence for a bimetallic epoxide enchainment" *J. Am. Chem. Soc.*, 2003; 125(39):11911-11924. Published online Sep. 3, 2003.
Papisov et al., "Semisynthetic Hydrophilic Polyals" *Biomacromolecules*, 2005: 6(5):2659-2670. Published online Aug. 18, 2005.
Park et al., *Biodegradable Hydrogels for Drug Delivery*, Lancaster, PA, 1993; cover page, title page, table of contents and p. 142.
Siepmann et al., "Mathematical modeling of bioerodible, polymeric drug delivery systems" *Adv. Drug Deliv. Rev.*, Jun. 2001; 48(2-3):229-247.
Stork et al., "The Enamine Alkylation and Acylation of Carbonyl Compounds" *J. Am. Chem. Soc.*, Jan. 1963; 85:207-222.
Uryu et al., "Selective Ring-Opening Polymerization of Di-O-methylated and Di-O-benzylated 1,4-Anhydro-α-D-ribopyranoses and Structure Proof of Synthetic Cellulose-Type Polysaccharide (1→4)-β-D-ribopyranan and (1→5)-α-D-ribofuranan" *J. Am. Chem. Soc.*, Nov. 1983; 105:6865-6871.
Uryu et al., "Ring-Opening Polymerization of 1,4-Anhydro-2,3,6-tri-O-benzyl-α-D-glucopyranose and 1,4-Anhydro-2,3,6-tri-O-benzyl-β-D-galactopyranose" *Macromolecules*, Jul. 1985; 18:599-605.
Vogel et al., *Vogel's Textbook of Practical Organic Chemistry*, New York, NY, Wiley, 1989; Fifth Edition, revised by Furniss et al.; cover page, title page, and table of contents only.
Wikipedia, "Glycolic Acid," [online]. [Retrieved on Jan. 25, 2006]. Retrieved from the Internet:<URL:http://en.wikipedia.org/wiki/Glycolic_acid>; Nov. 29, 2005; 1 pg.
Wikipedia, "Lactic Acid," [online]. [Retrieved on Jan. 25, 2006]. Retrieved from the Internet:<URL:http://en.wikipedia.org/wiki/Lactic_acid>; Jan. 25, 2006; 2 pgs.
Wikipedia, "Polyglycolide," [online]. [Retrieved on Jan. 25, 2006]. Retrieved from the Internet:<URL:http://en.wikipedia.org/wiki/Polyglycolide>; Apr. 13, 2005; 1 pg.
Wikipedia, "Polylactic Acid," [online]. [Retrieved on Jan. 25, 2006]. Retrieved from the Internet:<URL:http://en.wikipedia.org/wiki/Polylactic_acid>; Jan. 23, 2006; 2 pgs.
Yukovetskiy et al., "Fully degradable Hydrophilic Polyals for Protein Modification" *Biomacromolecules*, 2005; 6(5):2648-2658. Published online on Aug. 17, 2005.
"CellTiter-Glo® Luminescent Cell Viability Assay, Instructions for Use of Products G7570, G7571, G7572 and G7573", Promega Corporation, Madison, WI, revised Sep. 2005; 8 pgs.
"CellTiter 96® Aqueous One Solution Cell Proliferation Assay, Instructions for Use of Products G3580, G3581 and G3582", Promega Corporation, Madison, WI, revised Apr. 2005; 13 pgs.

(Continued)

*Primary Examiner*—Robert A Wax
*Assistant Examiner*—Lyndsey Beckhardt
(74) *Attorney, Agent, or Firm*—James H. Ackley; Kenneth J. Collier; Mueting, Raasch & Gebhardt (57) ABSTRACT

Polyketal polymers, and methods of making and using such polyketal polymers are disclosed herein. The polyketal poylmers can be useful for applications including, for example, medical devices and pharmaceutical compositions. In a preferred embodiment, the polyketal polymers are biodegradable.

31 Claims, 1 Drawing Sheet

OTHER PUBLICATIONS

Colonge et al., "The 1, 2, 5-Triols", *Bulletin de la Societe Chimique de France*, 1955; 836-838. (With English language abstract; 1 pg.).

Colonge et al., "Preparation of 5-alkyltetrahydrofurylcarbinols and their dehydration to 2-alkyl-2, 3-dihydro-4-pyrans", *Bulletin de la Societe Chimique de France*, 1962; 1166-71. (With English language abstract; 4 pgs.).

"CyQuant® Cell Proliferation Assay Kit" datasheet, Molecular Probes, Inc. (Invitrogen), Eugene, OR, revised Feb. 21, 2006; 7 pgs.

"CytoTox 96® Non Radioactive Cytotoxicity Assay, Instructions for Use of Product G1780", Promega Corporation, Madison, WI, revised Mar. 2006; 18 pgs.

Frauli, et al., "Inhibition of fibroblast proliferation in a culture of human endometrial stromal cells using a medium containing D-valine" *Archives of Gynecology and Obstetrics*, Jun. 1987; 241(2):87-96.

Hibbert et al., "Studies on cellulose chemistry: IV. Properties of gamma-delta-dihydroxy-carbonyl derivatives and their bearing on the polymerization of polysaccharides", *J. Am. Chem. Soc.*, 1923; 45:2433-2439.

U.S. Appl. No. 11/897,085, filed Aug. 29, 2007, Benz et al.

* cited by examiner

POLYKETAL POLYMERS, AND METHODS OF MAKING AND USING SAME

This application claims the benefit of U.S. Provisional Application No. 60/774,908, filed 17 Feb. 2006, which is hereby incorporated by reference in its entirety.

BACKGROUND

Biodegradable polymers have found uses in a wide variety of applications ranging from trash bags that decompose in landfills to implantable medical devices that biodegrade in the body. Most of these applications require that such polymers have adequate physical properties and stability to provide for suitable handling and utility prior to being subjected to end use conditions that promote biodegradation. Further, it is often preferable that these same polymers rapidly or controllably biodegrade once subjected to such end use conditions. In addition, it is often desired that biodegradable polymers used for implantable medical devices be converted under physiological conditions to materials that do not irritate or harm the surrounding tissue. Many biodegradable polymers known in the art lack the combination of physical and/or chemical properties desired to meet the needs for specific applications.

Current and new applications for biodegradable polymers continue to create a need for new polymers that provide some or all of the above-described properties.

SUMMARY

In one aspect, the present invention provides a method of preparing a polyketal polymer. In one embodiment, the method includes combining components including a polymerization agent and at least one cyclic oxygen-containing compound under conditions effective to polymerize the at least one cyclic oxygen-containing compound, wherein the at least one cyclic oxygen-containing compound is selected from the group consisting of: a compound of the formula (Formula I)

a compound of the formula (Formula II)

and combinations thereof; wherein: each X independently represents $NR^5$, $CR^5R^6$, $SiR^5R^6$, S, a sulfur-bonded group, a phosphorus-bonded group, or each Y independently represents O, $NR^5$, $CR^5R^6$, $SiR^5R^6$, S, a sulfur-bonded group, a phosphorus-bonded group, or each n is independently from 0 to 5; each $R^1$ independently represents an organic group; each $R^2$, $R^3$, $R^4$, $R^5$, and $R^6$ independently represents H or an organic group; and $R^1$, $R^2$, $R^3$, $R^4$, $R^5$, and/or $R^6$ can optionally be joined to each other to form one or more rings. The polymers and compositions including the polymers prepared by the above-disclosed illustrative method can be useful for applications including, for example, medical devices and pharmaceutical compositions. In a preferred embodiment, the polyketal polymers prepared thereby are biodegradable.

The presently disclosed methods of preparing polyketal polymers can offer advantages over other methods known in the art for preparing polyketals. For example, the presently disclosed methods are convenient for preparing polyketal polymers without the need to remove small molecule byproducts (e.g., water and other small molecules such as alcohols) typically formed in known condensation type polymerizations.

In another aspect, the present invention provides polyketal polymers. In one embodiment, the polymer includes two or more repeat units selected from the group consisting of: a repeat unit of the formula (Formula II):

a repeat unit of the formula (Formula IV):

and combinations thereof; wherein: each X independently represents $NR^5$, $CR^5R^6$, $SiR^5R^6$, S, a sulfur-bonded group, a phosphorus-bonded group, or each Y independently represents O, $NR^5$, $CR^5R^6$, $SiR^5R^6$, S, a sulfur-bonded group, a phosphorus-bonded group, or each n is independently from 0 to 5; each $R^1$ independently represents an organic group; each $R^2$, $R^3$, $R^4$, $R^5$, and $R^6$ independently represents H or an organic group; and $R^1$, $R^2$, $R^3$, $R^4$, $R^5$, and/or $R^6$ can optionally be joined to each other to form one or more rings.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

A wide variety of biodegradable and/or bioerodible polymers are known in the art. As used herein, "biodegradable" and "bioerodible" are used interchangably and are intended to broadly encompass materials including, for example, those that tend to break down upon exposure to physiological environments. Biodegradable and/or bioerodible polymers known in the art include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)); polyanhydrides; and poly(orthoesters). However, many of these polymers lack the combination of physical and/or chemical properties desired for certain applications, particularly in the medical and pharmaceutical fields.

For example, polyglycolide and polylactide homo- and co-polymers are converted under physiological conditions to products including glycolic acid and lactic acid, respectively. For certain medical device applications, the formation of acidic products can limit the utility of such biodegradable polymers. Further, many of the biodegradable polymers noted above biodegrade at a slower rate than desired for specific applications.

Certain polyketals are also known to be biodegradable polymers. As used herein, a "polyketal" refers to a homo- or co-polymer that includes two or more (i.e., a plurality) of ketal repeat units. As used herein, a "ketal" repeat unit is a unit including a ketal-containing group that is repeated in the polymer at least once. A ketal group is a group that includes an —O—C(M)(N)—O— functionality with the proviso that neither M nor N is hydrogen (e.g., an acetal-containing group) or oxygen (e.g., an orthoester-containing group).

Further, known methods for preparing some of the known biodegradable polymers noted above (including, for example, known polyketals) typically involve condensation type polymerizations that form small molecule byproducts (e.g., water and other small molecules such as alcohols) during the polymerization reaction. The presence of such small molecule byproducts in the reaction mixture can adversely impact the molecular weight of the resultant polymer, and removal of such small molecule byproducts during the polymerization process can lead to a more complicated and expensive process.

The limitations of known methods of making polyketals has limited the commercial use of such polymers. A typical known method includes, for example, condensing or reacting a diol with a ketone or ketal to form a polyketal in a step growth polymerization process. However, in preparing polymers in a step growth polymerization process that have sufficient molecular weight for certain medical device applications, the strict control of reactant stoichiometries and the concurrent removal of byproducts formed can lead to difficult, expensive, and/or poorly reproducible processes.

The presently disclosed methods of preparing polyketal polymers can offer advantages over other methods known in the art for preparing polyketals. For example, the presently disclosed methods can be convenient for preparing polyketal polymers without the need to remove small molecule byproducts (e.g., water and other small molecules such as alcohols) typically formed in known condensation type polymerizations.

In contrast, the present invention provides polyketal polymers and convenient methods of preparing such polymers. Notably the presently disclosed polyketals include polymers that are not converted under physiological conditions to acidic products. Further, the present invention provides polyketal polymers that can biodegrade at a sufficiently high rate to enable them to be considered for use in specific applications.

In one aspect, the present invention provides a method of preparing a polyketal polymer. In one embodiment, the method includes combining components including a polymerization agent and at least one cyclic oxygen-containing compound under conditions effective to polymerize the at least one cyclic oxygen-containing compound. Preferably, the method can form high molecular weight polymers. Typically, the polymerization proceeds by a ring opening polymerization process, although isomerizations of rings are also possible during the polymerization process. Ring opening polymerizations are typically advantageous in that molecular weight can be readily controlled by variables including, for example, the ratio of polymerization agent to monomer. Typically the polymerization can be initiated thermally in the presence of a suitable polymerization agent. Typically, the polymerization process proceeds through a cationic, an anionic, a free radical, and/or an organometallic pathway.

Cyclic oxygen-containing compounds useful in the present method include at least one compound selected from the group consisting of:

a compound of the formula (Formula I)

a compound of the formula (Formula II)

and combinations thereof; wherein: each X independently represents $NR^5$, $CR^5R^6$, $SiR^5R^6$, S, a sulfur-bonded group (i.e., an organic or inorganic group bonded through sulfur such as, for example, S(O), S(O)$_2$, or the like), a phosphorus-bonded group (i.e., an organic or inorganic group bonded through phosphorus such as, for example, PR or PR$_3$, where R is an organic group, or the like), or each Y independently represents O, $NR^5$, $CR^5R^6$, $SiR^5R^6$, S, a sulfur-bonded group, a phosphorus-bonded group, or each n is independently from 0 to 5; each $R^1$ independently represents an organic group; each $R^2$, $R^3$, $R^4$, $R^5$, and $R^6$ independently represents H or an organic group; and $R^1$, $R^2$, $R^3$, $R^4$, $R^5$, and/or $R^6$ can optionally be joined to each other to form one or more rings. The wavy bonds in the formulas herein are used to indicate unspecified stereochemistry.

In certain embodiments, each X and Y independently represents $CR^5R^6$; each n is 1; each $R^1$ independently represents a C1-C10 organic group; each $R^2$, $R^3$, $R^4$, $R^5$, and $R^6$ independently represents H or a C1-C10 organic group; and $R^1$ and $R^5$ can optionally be joined to each other to form a ring.

In other certain embodiments, each X and Y independently represents $CR^5R^6$; each n is 1; each $R^1$ independently represents a phenyl group (and preferably a phenyl ring) or a C1-C4 aliphatic or alicyclic group (a preferably a C1-C4 aliphatic or alicyclic moiety); each $R^2$, $R^3$, $R^4$, $R^5$, and $R^6$ independently represents H, a phenyl group, or a C1-C4 aliphatic or alicyclic group (and preferably H, a phenyl group, or a C1-C4 aliphatic or alicyclic moiety); and $R^1$ and $R^5$ can optionally be joined to each other to form a five- or six-membered ring.

In one preferred embodiment, the cyclic oxygen-containing compound is 5,6-epoxy-hexan-2-one (i.e., Formula I, wherein $R^1$=methyl; X=Y=CH$_2$; n=1; and $R^2$=$R^3$=$R^4$=H). In another preferred embodiment, the cyclic oxygen-containing compound is 1-phenyl-4,5-epoxy-pentan-1-one (i.e., Formula I, wherein $R^1$=phenyl; X=Y=CH$_2$; n=1; and $R^2$=$R^3$=$R^4$=H).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for monomers and polymers of this invention are those that do not interfere with the ring opening polymerization reaction disclosed herein. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Thus, in cyclic oxygen-containing compounds of Formula I and Formula II as disclosed herein above (e.g., wherein each X independently represents $NR^5$, $CR^5R^6$, $SiR^5R^6$, S, a sulfur-bonded group, a phosphorus-bonded group, or each Y independently represents O, $NR^5$, $CR^5R^6$, $SiR^5R^6$, S, a sulfur-bonded group, a phosphorus-bonded group, or each n is independently from 0 to 5; each $R^1$ independently represents an organic group; each $R^2$, $R^3$, $R^4$, $R^5$, and $R^6$ independently represents H or an organic group; and $R^1$, $R^2$, $R^3$, $R^4$, $R^5$, and/or $R^6$ can optionally be joined to each other to form one or more rings), any of the R substituents that are "organic groups" can include as at least a portion thereof, for example, a cyclic oxygen-containing functionality (e.g., at least a portion of Formula I or Formula II); an imagable functionality (i.e., a functionality visible in an imaging system, such as, for example, one or more radiopaque functionalities such as iodinated groups, ferromagnetic functionalities, and magnetic susceptible functionalities such as Fe, Cr, Ni, and Gd); a latent reactive functionality (e.g., ethylenic unsaturation and/or oxygen-containing rings suitable for latent crosslinking after polymerization); or combinations thereof. Thus, the cyclic oxygen-containing compounds of Formula I and Formula II as disclosed herein above include not only monofunctional compounds, but additionally di- and poly-functional compounds.

Monomers of Formula I and II can be prepared by suitable methods known to one of skill in the art. For example, a monomer of Formula I can be prepared by epoxidation of the corresponding ethylenically unsaturated compound. For another example, a monomer of Formula II can be prepared by dehydration of dihydroxyketone compounds and/or thermal treatment (e.g., heating under vacuum) a compound of Formula I.

A single cyclic oxygen-containing monomer as described herein can be used to prepare a homopolymer as disclosed herein. Similarly, a cyclic oxygen-containing monomer as described herein can be used in combination with one or more additional monomers to prepare a copolymer as disclosed herein. The one or more additional monomers can be different cyclic oxygen-containing monomer(s) as disclosed herein, or monomers that are not cyclic oxygen-containing monomers (e.g., lactides, glycolides, butyrolactones, valerolactones, caprolactones, cyclic carbonates such as trimethylene carbonate and 1,2-o-isopropylidene-[D]-xylofuranose-3,5-cyclic carbonate, cyclic ethers such as ethylene oxide, cyclic acetals such as 1,3-dioxolane, and combinations thereof). The monomers used to prepare the homo- and co-polymers disclosed herein can be monofunctional, difunctional, or polyfunctional; or a combination of such monomers can be used.

In some embodiments, copolymers can be formed by starting with an oligomeric or polymeric macromolecule (e.g., polyethylene glycol) and forming polyketal blocks thereon by the polymerization of the monomers described herein. In other embodiments, copolymers can be formed by starting with a polyketal polymer and reacting the polyketal polymer with additional monomers, oligomers, polymers, and/or other reactive compounds.

A polymerization agent can be used to initiate and/or propagate the polymerization reaction. A wide variety of polymerization agents can be used that are known in the art to catalyze ring opening polymerizations. Typically, the polymerization agent provides for polymerization through a cationic, an anionic, a free radical, and/or an organometallic pathway. The polymerization agent may be present in catalytic amounts, or alternatively, may be used in stoichiometric amounts with partial or total consumption of the polymerization agent during the polymerization reaction.

In some embodiments, the polymerization agent includes a Lewis acid or a Brønsted-Lowry acid. Suitable Lewis acids typically include one or more elements such as Al, Fe, B, Zn, Sb, Ti, Cu, Sn, Si, and the like. Examples of suitable Lewis acids include, for example, boron trifluoride and/or boron trifluoride etherate, zinc chloride, zinc iodide, stannous 2-ethylhexanoate, zinc trifluoromethanesulfonate (i.e., zinc triflate), trimethylsilyl triflate, antimony pentachloride, and the like, and combinations thereof.

Suitable Brønsted-Lowry acids include, for example, hydrochloric acid, p-toluenesulfonic acid, methanesulfonic acid, trifluoromethanesulfonic acid, camphorsulfonic acid, and the like.

In some embodiments, the polymerization agent includes an organometallic compound or a metal salt. Suitable organometallic compounds include zinc-containing compounds (e.g., diethyl zinc) and those disclosed, for example, in U.S. Pat. No. 6,133,402 (Coates et al.); Moore et al., *J. American Chem. Soc.*, 125:11911-11924 (2003); and the like. Suitable metal salts include, for example, metal halides (e.g., metal chlorides, metal bromides, metal iodides, and combinations thereof), metal pseudohalides (e.g., metal cyanates, metal thiocyanates, metal isothiocyanates, metal isocyanides, metal azides, metal thiosulfates, and combinations thereof), metal sulfonates (e.g., metal triflates, metal mesylates, metal p-toluenesulfonates, metal camphorsulfonates, and combinations thereof), metal carboxylates (e.g., stannous 2-ethylhexanoate and metal perfluorocarboxylates), metal carbonates (e.g., cesium carbonate), and combinations thereof. The metal salts typically include a metal such as Zn, Cs, or combinations thereof.

Certain polymerization agents that are known to be useful in ring-opening polymerizations can be particularly advantageous for preparing copolymers from monomers as disclosed herein with other monomers such as, for example, lactides, glycolides, butyrolactones, valerolactones, caprolactones, cyclic carbonates, cyclic ethers, cyclic acetals, and combinations thereof. For example, metal-containing catalysts such as stannous 2-ethylhexanoate or diethylzinc can be useful in preparing (e.g., at an elevated temperature) a copolymer of trimethylene carbonate with 5,6-epoxy-hexan-2-one (99:1 molar ratio), a copolymer that can have bulk physical properties similar to those of poly(trimethylene carbonate), but with hydrolysis properties similar to those of polyketals.

The ratio of the polymerization agent to the monomers can be varied as desired, and is typically selected to provide the desired reaction time at the selected reaction temperature for the specific polymerization agent. The ratio of the polymerization agent to the monomers can also be varied to influence the molecular weight of the resulting polymers, with lower ratios typically resulting in higher molecular weights. In some embodiments, at least 0.0000001 mole %, sometimes at least 0.000001 mole %, and other times at least 0.00001 mole % of polymerization agent is used, based on the total moles of monomers and polymerization agents. In some embodiments, at most 30 mole %, sometimes at most 20 mole %, and other times at most 10 mole % of polymerization agent is used, based on the total moles of monomers and polymerization agents.

Suitable polymerization agents may be monofunctional (i.e., capable of initiating one polymer chain), difunctional (i.e., capable of initiating two polymer chains), or polyfunctional (i.e., capable of initiating more than two polymer chains). For cases in which the polymerization agent is incorporated into the polymer chain, polyfunctional polymerization agents can lead to highly branched polymer structures (e.g., star structures).

In certain embodiments, components including the one or more monomers and the polymerization agent can be combined neat (e.g., without adding a solvent). In other certain embodiments, components including the one or more monomers and the polymerization agent can be combined in a dry organic solvent at a concentration selected to provide a convenient reaction rate. Typically and preferably, at least a portion of the components are combined under an inert atmosphere. The reaction temperature can be selected and/or varied as desired to provide a convenient reaction rate.

The polymerization methods disclosed herein can provide polyketal polymers. In one embodiment, the polymer includes two or more repeat units selected from the group consisting of:

a repeat unit of the formula (Formula III):

a repeat unit of the formula (Formula IV):

and combinations thereof; wherein: each X, Y, n, $R^1$, $R^2$, $R^3$, and $R^4$ is defined as disclosed herein above for the corresponding monomers. In one preferred embodiment, $R^1$=methyl; X=Y=$CH_2$; n=1; and $R^2$=$R^3$=$R^4$=H. In another preferred embodiment, $R^1$=phenyl; X=Y=$CH_2$; n=1; and $R^2$=$R^3$=$R^4$=H.

Notably, $R^1$ in each of the polyketal repeating units disclosed herein represents an organic group which is advantageous in providing polymers with useful biodegradability. In contrast, polysaccharides are structures in which $R^1$ represents hydrogen. Although polysaccharides are useful biomaterials (e.g., useful in biomedical applications), they typically do not substantially biodegrade in physiologic environments.

In the above-disclosed polymers, any of the R substituents that are "organic groups" can include as at least a portion thereof, for example, a cyclic oxygen-containing functionality (e.g., at least a portion of Formula I or Formula II); an imagable functionality (e.g., one or more radiopaque functionalities such as iodinated groups, ferromagnetic functionalities, and magnetic susceptible functionalities such as Fe, Cr, Ni, and Gd); a latent reactive functionality (e.g., ethylenic unsaturation and/or oxygen-containing rings suitable for latent crosslinking after polymerization); or combinations thereof.

The polymers disclosed herein can include a single cyclic oxygen-containing repeat unit (i.e., a homopolymer), or two or more different repeat units (i.e., a copolymer). In such copolymers, the two or more different repeat units can all be different cyclic oxygen-containing repeat units of Formula III and/or Formula IV, or alternatively, one or more cyclic oxygen-containing repeat units of Formula III and/or Formula IV in combination with one or more repeat units that are not of Formula III or Formula IV (e.g., lactide repeat units, glycolide repeat units, butyrolactone repeat units, valerolactone repeat units, caprolactone repeat units, cyclic carbonate repeat units such as trimethylene carbonate and 1,2-o-isopropylidene-[D]-xylofuranose-3,5-cyclic carbonate, cyclic ether repeat units such as ethylene oxide, cyclic acetals such as 1,3-dioxolane, and combinations thereof). The polymers disclosed herein can be linear polymers, crosslinkable polymers, and/or crosslinked polymers.

Copolymers as disclosed herein can be random copolymers, alternating copolymers, block copolymers, graft copolymers, or combinations thereof. For example, mixtures of monomers can be combined with a polymerization agent to prepare random and/or alternating copolymers. For another example, one or more monomers can be combined with a polymerization agent and allowed to react until all the monomer is consumed, followed by the addition of one or more different monomers, and optionally additional polymerization agent (which can be the same or different than the first polymerization agent), which are then allowed to react to prepare block and/or graft copolymers.

Block copolymers in which at least one block of the block copolymer is a polyketal block including two or more repeat units selected from the group consisting of repeat units of Formula III, repeat units of Formula IV, and combinations thereof, can be of particular interest for certain applications. The at least one other block of such block copolymers can be selected from blocks having a wide variety of repeat units including, for example, alpha-hydroxy alkanoates, beta-hydroxy alkanoates, gamma-hydroxy alkanoates, delta-hydroxy alkanoates, epsilon-hydroxy alkanoates, or combinations thereof. In certain embodiments, the at least one other block of such block copolymers can be a poly(orthoester) block. In other certain embodiments, the at least one other block of such block copolymers can be a poly(alkyleneglycol) block including alkylene glycol repeat units.

Typically and preferably, the polyketal polymers disclosed herein are biodegradable. Typically, the average molecular weight (and preferably the weight average molecular weight) of the polymers disclosed herein is at least 1000 Daltons, and sometimes at least 2000 Daltons, 5,000 Daltons, or even 10,000 Daltons or more. Average molecular weights of the polymers disclosed herein can be as high as desired for specific applications. Typically, the average molecular weight (and preferably the weight average molecular weight) of the polymers disclosed herein is at most 10,000,000 Daltons, and sometimes at most 5,000,000 Daltons, 2,000,000 Daltons, or even 1,000,000 Daltons. Typically the polydispersity index of the polymers disclosed herein is at most 3, and sometimes at most 2.5, and other times at most 2.0.

For certain applications, a polyketal polymer as disclosed herein can be blended with another polymer (e.g., the same or different than the polyketal polymers disclosed herein) to provide the desired physical and/or chemical properties. For example, two polyketal polymers having different molecular weights can be blended to optimize the release rate of a biologically active agent. For another example, two polyketal polymers having different repeat units can be blended to provide desired physical and/or chemical properties. For even another example, a polyketal polymer can be blended with another polymer that is not a polyketal polymer to provide desired physical and/or chemical properties.

Polyketal polymers as disclosed herein can be used in various combinations for various applications. They can be used as tissue-bulking agents in urological applications for bulking the urinary sphincter to prevent stress incontinence or in gastrological applications for bulking of the lower esophageal sphincter to prevent gastroesophageal reflux disease. They can be used for replacements for nucleus pulposis or repair of annulus in intervertebral disc repair procedures. They can be used as tissue adhesives or sealants. They can be used as surgical void fillers, for example, in reconstructive or cosmetic surgery (e.g., for filling a void after tumor removal). They can be used to repair aneurysms, hemorrhagic stroke or other conditions precipitated by failure of a blood vessel. They can be used to prevent surgical adhesions. Polyketal polymers as disclosed herein can further be used for applications such as scaffolds or supports for the development and/or growth of cells for applications including, for example, tissue engineering and the fabrication of artificial organs.

Polyketal polymers as disclosed herein can be used in injectable compositions. Such injectable compositions could be used as tissue bulking agents (e.g., for the treatment of urinary stress incontinence, for the treatment of gastroesophageal reflux disease, or serving to augment a degenerated intervertebral disc), void fillers (e.g., in cosmetic or reconstructive surgery, such as serving as a replacement for the nucleus pulposis), or as an injectable drug delivery matrix.

In some embodiments, no additives would be needed to form an injectable composition. In some embodiments, one or more polymers can be combined with a solvent such as N-methyl-2-pyrrolidone or dimethylsulfoxide (DMSO), which are fairly biocompatible solvents. The solvent can diffuse away after injection and the polymer can remain in place. Such injectable materials can be applied to a desired site (e.g., a surgical site) using a syringe, catheter, or by hand.

Also, injectable compositions could include crosslinkers (such as dicrylates), plasticizers (such as triethyl citrate), lipids (soybean oil), poly(ethylene glycol) (including those with the ends blocked with methyls or similar groups), silicone oil, partially or fully fluorinated hydrocarbons, N-methyl-2-pyrrolidone, or mixtures thereof.

Polymers of the present invention can be used in combination with a variety of particulate materials. For example, they can be used with moisture curing ceramic materials (e.g., tricalcium phosphate) for vertebroplasty cements, bone void filling (due to disease such as cancer or due to fracture). They can be used in combination with inorganic materials such as hydroxylapatite to form pastes for use in bone healing, sealing, filling, repair, and replacement. They can be used as or in combination with polymer microspheres that can be reservoirs for a biologically active agent such as a protein, DNA plasmid, RNA plasmid, antisense agent, etc.

Alternatively, polyketals of the present invention can be used in combination with other materials to form a composite (e.g., a polymer having an additive therein). In addition to one or more polyketals, composites can include a wide variety of additives, and particularly particulate additives, such as, for example, fillers (e.g., including particulate, fiber, and/or platelet material), other polymers (e.g., polymer particulate materials such as polytetrafluoroethylene can result in higher modulus composites), imaging particulate materials (e.g., barium sulfate for visualizing material placement using, for example, fluoroscopy), biologically derived materials (e.g., bone particles, cartilage, demineralized bone matrix, platelet gel, and combinations thereof), and combinations thereof.

Additives can be dissolved, suspended, and/or dispersed within the composite. For particulate additives, the additive is typically dispersed within the composite.

Polyketals of the present invention can be combined with fibers, woven or nonwoven fabric for reconstructive surgery, such as the in situ formation of a bone plate or a bone prosthesis.

In certain embodiments, one or more polyketal polymers as disclosed herein can be shaped to form a medical device, preferably a biodegradable medical device. The one or more polymers can be shaped by methods known in the art including compression molding, injection molding, casting, extruding, milling, blow molding, or combinations thereof. As used herein, a "medical device" includes devices that have surfaces that contact tissue, bone, blood, or other bodily fluids in the course of their operation, which fluids are subsequently used in patients. This can include, for example, extracorporeal devices for use in surgery such as blood oxygenators, blood pumps, blood sensors, tubing used to carry blood, and the like which contact blood which is then returned to the patient. This can also include endoprostheses implanted in blood contact in a human or animal body such as vascular grafts, stents, pacemaker leads, heart valves, and the like, that are implanted in blood vessels or in the heart. This can also include devices for temporary intravascular use such as catheters, guide wires, and the like which are placed into the blood vessels or the heart for purposes of monitoring or repair. A medical device can also be fabricated by polymerizing components including monomers of Formula I and/or Formula II in a suitable mold.

Polyketal polymers as disclosed herein can also be coated onto a substrate if desired. A coating mixture of the polymer can be prepared using solvents such as toluene, chloroform, tetrahydrofuran, perfluorinated solvents, and combinations thereof. Preferred solvents include those that can be rendered moisture-free and/or those that have no active hydrogens. The coating mixture can be applied to an appropriate substrate such as uncoated or polymer coated medical wires, catheters, stents, prostheses, penile inserts, and the like, by conventional coating application methods. Such methods include, but are not limited to, dipping, spraying, wiping, painting, solvent swelling, and the like. After applying the coating solution to a substrate, the solvent is preferably allowed to evaporate from the coated substrate.

The materials of a suitable substrate include, but are not limited to, polymers, metal, glass, ceramics; composites, and multilayer laminates of these materials. The coating may be applied to metal substrates such as the stainless steel used for guide wires, stents, catheters and other devices. Organic substrates that may be coated with the polymers of this invention include, but are not limited to, polyether-polyamide block copolymers, polyethylene terephthalate, polyetherurethane, polyesterurethane, other polyurethanes, silicone, natural rubber, rubber latex, synthetic rubbers, polyester-polyether copolymers, polycarbonates, and other organic materials.

Additives that can be combined with a polyketal polymer as disclosed herein to form a composition include, but are not limited to, wetting agents for improving wettability to hydrophobic surfaces, viscosity and flow control agents to adjust the viscosity and thixotropy of the mixture to a desired level, antioxidants to improve oxidative stability of the coatings, dyes or pigments to impart color or radiopacity, and air release agents or defoamers, cure catalysts, cure accelerants, plasticizers, solvents, stabilizers (cure inhibitors, pot-life extenders), and adhesion promoters.

Of particular interest for medical and pharmaceutical applications are compositions that include one or more polyketal polymers as disclosed herein and a biologically active agent. As used herein, a "biologically active agent" is intended to be broadly interpreted as any agent capable of eliciting a response in a biological system such as, for example, living cell(s), tissue(s), organ(s), and being(s). Biologically active agents can include natural and/or synthetic agents. Thus, a biologically active agent is intended to be inclusive of any substance intended for use in the diagnosis, cure, mitigation, treatment, or prevention of disease or in the enhancement of desirable physical or mental development and conditions in a subject. The term "subject" as used herein is taken to include humans, sheep, horses, cattle, pigs, dogs, cats, rats, mice, birds, reptiles, fish, insects, arachnids, protists (e.g., protozoa), and prokaryotic bacteria. Preferably, the subject is a human or other mammal.

A preferred class of biologically active agents includes drugs. As used herein, the term "drug" means any therapeutic agent. Suitable drugs include inorganic and organic drugs, without limitation, and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems (including urological systems), histamine systems, and the like. Such conditions, as well as others, can be advantageously treated using compositions as disclosed herein.

Preferred classes of drugs include, for example, Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

Suitable drugs can have a variety of uses including, but are not limited to, anticonvulsants, analgesics, antiparkinsons, antiinflammatories (e.g., ibuprofen, fenbufen, cortisone, and the like), calcium antagonists, anesthetics (e.g., benoxinate, benzocaine, procaine, and the like), antibiotics (e.g., ciprofloxacin, norfloxacin, clofoctol, and the like), antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, and the like.

Specific examples of drugs include those selected from the group consisting of salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, clonidine, and combinations thereof.

Compositions including a biologically active agent and a polyketal polymer as disclosed herein and can be prepared by suitable methods known in the art. For example, such compositions can be prepared by solution processing, milling, extruding, polymerizing components including monomers of Formula I and/or Formula II in the presence of a biologically active agent, and combinations thereof.

Compositions including polyketal polymers as disclosed herein (e.g., with or without a biologically active agent) can further include additional components. Examples of such additional components include fillers, dyes, pigments, inhibitors, accelerators, viscosity modifiers, wetting agents, buffering agents, stabilizers, biologically active agents, polymeric materials, excipients, and combinations thereof.

Medical devices that include one or more polyketal polymers as disclosed herein and a biologically active agent can have a wide variety of uses. In such devices, the biologically active agent is preferably disposed in the one or more polymers. As used herein, the term "disposed" is intended to be broadly interpreted as inclusive of dispersed, dissolved, suspended, or otherwise contained at least partially therein or thereon.

For example, such devices can be used to deliver a biologically active agent to a tissue by positioning at least a portion of the device including the one or more polymers proximate the tissue and allowing the one or more polymers to biodegrade and deliver the biologically active agent disposed therein. For another example, such devices can be used to control the release rate of a biologically active agent from a medical device by disposing the biologically active agent in at least one of the one or more polymers.

The present invention is illustrated by the following examples. It is to be understood that the particular examples, materials, amounts, and procedures are to be interpreted broadly in accordance with the scope and spirit of the invention as set forth herein.

EXAMPLES

Example I

Synthesis of 5,6-epoxy-hexan-2-one 5,6-Epoxy-hexan-2-one was prepared similar to a reported method by Broshears et al., *Journal of Chemical Education*, 81:1018-1019 (2004), by reacting hexen-2-one with oxone in acetone buffered with sodium hydrogen carbonate. The product was purified by vacuum distillation, having a boiling point about 33° C. to 35° C. at a pressure of 0.5 mmHg. The yield is about 59 mole percent. NMR ($CDCl_3$, δ): 100 mHz $^{13}$C-NMR, 207.73, 51.41, 47.24, 39.45, 29.98, 26.30; 400 mHz, $^1$H-NMR, 1.62 (1H, m); 1.95 (1H, m); 2.1 (3H, s), 2.46 (1H, m), 2.57 (2H, m), 2.58 (1H, m), 2.95 (1H, m). All the epoxy ketone monomers disclosed herein were prepared in a similar manner.

Example II

Synthesis of 1-phenyl-4-pentene-1-one

Ethyl benzoylacetate (38.4 g, 0.2 mole, Aldrich) was added to a mixture of sodium ethoxide (13.6 g, 0.2 moles) in 200 mL ethanol. The mixture was stirred magnetically and slowly brought to reflux. After 30 minutes, the reaction mixture was cooled and allyl bromide (26.6 g, 0.22 moles, Aldrich) was added via a syringe with care (10 minutes), and the mixture was refluxed for another 2 hours. After cooling to room temperature, the mixture was transferred to a separatory funnel and diluted with 300 mL saturated sodium bicarbonate and extracted with ether (200 mL×3). The combined ether layer was washed with brine and dried over anhydrous magnesium sulfate. The solvent was removed by rotary evaporation resulting in a brownish oil. Without further purification, the crude product was suspended in 250 mL 1 normal sodium hydroxide solution and brought to gentle reflux overnight. After cooling, the oil that floated on top was separated and was combine with the organic layer from the extractions that followed. The aqueous layer was acidified with 50% sulfuric acid to pH 1 and heated to reflux for 5 hours. The mixture was extracted with ethyl acetate (200 mL×3). The organic layer was dried over sodium sulfate and the solvent removed by rotary evaporation to yield a yellow oil. Yield: 19.7 g (61.5%) with boiling point 70-80° C. at 0.8 mmHg. $^1$H-NMR (CDCl$_3$, δ): phenyl ring (7.97, d, 2H, 7.55, m, 1H, 7.4, m, 2H); vinyl group (5.8, m 2H, 5.1 q, 1H); 3.08 (t, 2H); 2.5 (m, 2H). See also, Vogel et al., *Vogel's Textbook of Practical Organic Chemistry*. Fifth Edition, revised by Furniss et al., 1989, Pearson Prentice Hall).

1-phenyl-4,5-epoxypentan-1-one: A white solid recrystallized from ether and hexane. $^1$H-NMR (CDCl$_3$, δ): phenyl ring (7.96, d, 2H, 7.55, t; 1H, 7.46, t, 2H); 3.16 (t, 2H); 3.08 (m, 1H); 2.5 (2.79 t, 1H); 2.55 (d, 1H); 2.17 (m, 1H); 1.83 (m, 1H). 13C-NMR: 199.1, 136.8, 133.3, 128.7, 128.1, 51.6, 47.4, 34.6, 26.8.

Example III

Synthesis of 5-methyl-5-hexen-2-one

Pentadione (75 g, 0.75 moles, Aldrich), 3-chloro-2-methyl propene (63.4 g, 0.70 moles, Aldrich) and potassium carbonate (96.3 g) were added to a dry 1 liter flask with 500 mL HPLC grade 200 proof ethanol. The mixture was stirred and heated to reflux for 18 hours. After brief cooling, the condenser was replaced by a distillation head. Heat was resumed to distill until about 370 mL ethanol and ethyl acetate were collected. The flask was allowed to cool to room temperature and into it ice water (550 mL) was added to dissolve the white slurry salts. Extraction (200 mL of ether, three times), wash with brine and drying over sodium sulfate, and finally rotary evaporation yielded a clear liquid. Distillation (145-155° C.) yielded 40 grams product (51%). $^1$H-NMR (CDCl$_3$, δ): 1.69 (s, 3H); 2.10 (s, 3H), 2.25 (t, 2H), 2.56 (t, 2H), 4.63 (s, 1H), 4.70 (s, 1H). 13C-NMR: 22.7, 29.9, 31.5, 41.9, 110.2, 144.4, 208.4. See also, Vogel et al., *Vogel's Textbook of Practical Organic Chemistry*. Fifth Edition, revised by Furniss et al., 1989, Pearson Prentice Hall).

1,4-dimethy-2,7-dioxabicyclo [2,2,1]heptane. Epoxidation of 5-methyl-5-hexen-2-one yielded isomerized bicyclic product: $^1$H-NMR (CDCl$_3$, δ): 1.44 (s, 3H); 1.52 (s, 3H); 1.62 (m, 1H); 1.75 (m, 2H); 1.87 (m, 1H); 3.27 (m, 1H); 3.60 (d, 1H). 13C-NMR: 17.2, 18.4, 35.0, 37.6, 75.5, 84.0, 108.3.

Example IV

Synthesis of 5-hepten-2-one

The synthesis was similar to that used for 5-methyl-5-hexen-2-one. Materials that were used: pentadione (108 g, 1.44 moles, Aldrich), crotyl chloride (94 g, 1.04 mol, Aldrich), potassium carbonate (139 g, 1.04 mole) and ethanol (700 mL). Product: 60-70° C., 65 mmHg (50° C., 11 mmHg), 68 g (58%). $^1$H-NMR (CDCl$_3$, δ), 1.61 (m, 3H), 2.11 (s, 3H), 2.25 (m 2H); 2.45 (t, 2H), 5.44 (m, 2H).

5,6-epoxy-heptan-2-one: Boiling point: 45-50° C., 0.4-0.5 mmHg, $^1$H-NMR (CDCl$_3$, δ), 1.24 (d, 3H), 1.59 (m, 1H), 1.95 (m, 1H); 2.55 (t, 2H), 2.64 (m, 1H), 2.74 (m, 1H).

Example V

Synthesis of 6-phenyl-5-hexen-2-one

The synthesis was similar to that used for 5-methyl-5-hexen-2-one. Materials that were used: cinnamyl chloride (100 g, 0.655 mole, Acros Organic), pentadione (72 g, 0.72 mole), and ethanol (460 mL). Product, 70-75° C., 0.1 mmHg, 48 g (42%). $^1$H-NMR (CDCl$_3$, δ): 2.15 (s, 3H); 2.16 (m, 2H); 2.60 (m, 2H); 6.17 (m, 1H), 6.42 (d, 1H), 7.2-7.33 (m, 5H).

5,6-epoxy-6-phenyl-hexan-2-one: $^1$H-NMR (CDCl$_3$, δ): 1.81 (m, 1H); 2.01 (m, 1H), 2.17 (s, 3H); 2.63 (t, 2H), 2.99 (m, 1H), 2.52 (d, 1H), 7.23-7.30 (m, 5H). $^{13}$C-NMR: 26.2, 30.0, 39.4, 58.8, 61.9, 125.6, 128.2, 128.5, 137.5, 207.5.

Example VI

Synthesis of 2-allyl cyclohexanone

Into a 2 liter round bottom flask, equipped with Dean-Stark water separator, cyclohexanone (186 g, 1.90 moles, Aldrich) was dissolved in 1 liter toluene, and then pyrrolidine (292 g, 4.1 moles) was added. The mixture was brought to reflux overnight, during which 55 mL of water was collected. After switching to a distillation head, excess pyrrolindine and toluene were distilled off (1.2 liter). When most of the volatiles had been removed, aspirator vacuum was applied to assist in removal of residual toluene. In the same flask, the residue was dissolved in 1.2 liter of acetonitrile. Allyl bromide (305 g, 2.5 moles) was added dropwise. The mixture was heated slowly to gentle reflux overnight. After distilling off most of the acetonitrile and cooling, 1.2 liter of water was added and heated to reflux for 30 minutes. Extracted with ether after the mixture was cooled (200 mL×3). Combined ether layer was dried over sodium sulfate. The crude product, after removing the solvent, was purified by vacuum distillation: 73-78° C., 6.7 mmHg, Yield: 156 grams (59% for two steps). See also, Stork et al., *J. American Chem. Soc.*, 85:207-222 (1963), and Johnson et al., *J. American Chem. Soc.*, 88:149-159 (1966).

2-(2',3'-epoxypropyl)-cyclohexan-1-one: The epoxide was prepared using a method similar to the method reported above in Example I. Yield: 29.8%.

Example VII

Synthesis of 2-allyl cyclopentanone 2-allyl cyclopentanone was prepared using a method similar to the method reported above for 2-allyl cyclohexanone. Yield: 7.5% for two steps.

Example VIII

Synthesis of o-vinyl acetophenone

Into a 3 necked 500 mL round bottom flask, equipped with a cooling condenser, a self equalizing addition funnel and a rubber septum, methyl triphenyl phosphonium bromide (54.5 g, 0.153 moles, Aldrich) was suspended in THF (120 mL). After flashing with nitrogen for 30 minutes, the flask was cooled to 0° C. n-Butyl lithium (61 mL, 2.5 M in hexane, 153 mmole) was added via a syringe. After stirring for 1.5 hours, a solution of 2-bromobenzaldehyde (25.0 g, 135.1 mmole) in THF (100 mL) was dripped into the flask slowly (2 hours). After stirred for 48 hours, the reaction mixture was quenched with brine (250 mL). The aqueous layer was extracted with toluene (100 mL×2). The toluene layer was diluted with hexane to precipitate triphenylphosphine oxide. After rotary evaporating off the solvent, the crude product was purified by column chromatography (silica gel 60-200 mesh), with 100% hexane as eluding solvent. First fraction, yield 11.5 g (41%). 8.8 Grams (48 mmole) of o-bromostyrene was used for the next reaction. Into a 3-necked round bottom flask fitted with condenser, self-equalizing funnel, a stopper and charged with magnesium (10 g, pre-activated), o-bromostyrene in 30 mL THF was added to cover Mg. After initiation of the reaction, the rest of bromide solution was added slowly and the mixture was refluxed for 1.5 hours. Into another 3-necked flask, acetic anhydride (10 g, 98 mmole) was dissolved in THF (30 mL) and the flask was cooled with dry ice/isopropanol. The Grignard reagent was transferred slowly (circa 1 hour) via a cannula needle and the mixture was stirred for 2.5 hours at $-70°$ C. After allowing to warm to room temperature, the mixture was then quenched with aqueous ammonium chloride and extracted with ethyl acetate (100 mL×2). After washing with water, dried over sodium sulfate and removal of the solvent, yellow oil was obtained. Yield: 6.5 gram (93%). $^1$H-NMR (CDCl$_3$, δ): 5.3 (d, 1H), 5.6 (d, 1H); 7.2 (q, 1H), 7.3 (t, 1H), 7.4 (t, 1H); 7.55 (d, 1H); 7.6 (d, 1H). 13C-NMR: 30, 116, 127, 128, 130, 132, 136, 137.5, 138, 201. Epoxidation using a method similar to that described above did not provide a clean product.

Example IX

Typical Polymerization Procedure

All glassware used for polymerizations was rinsed, successively, with 0.1 normal sodium hydroxide, water and acetone and dried in 110° C. oven overnight. The reaction was carried out in a glove box under an inert atmosphere. Zinc iodide (70 mg, 0.22 mmole, Aldrich) was dissolved in tetrahydrofuran (THF) (5 mL) upon stirring, and 5,6-epoxy-hexan-2-one (2.5 g, 22.9 mmole) was added and stirred without heating. After two days, the reaction mixture was dissolved in THF (with a drop of triethylamine) and precipitated from petroleum ether thrice at $-40°$ C. The resulting semisolid was dried under vacuum at 40° C. for two days before characterization. Yield: 1.6 g (64%). $^1$H-NMR (THF-d$_8$ δ; 4.2 (b, 1H); 3.7 (b, m, 2H); 2.1 (b, m, 4H); 1.4 (s, 3H). 13C-NMR: 107.3, 79.4, 65, 38.7, 29, 22.1. (Peaks at lower intensity: 77.9, 64, 37.6, 27.5, 22.1 may be due to the presence of syn/anti isomers).

Example X

Synthesis of Copolymers 5,6-Epoxy hexan-2-one (2.3 g) and 1-phenyl-4,5-epoxy-pentan-1-one (2.0 g) was dissolved in methylene chloride (5 mL). Six milliliters of zinc triflate (0.5% in CH$_2$Cl$_2$) was added to initiate the reaction.

Example XI

Typical properties of homopolymers and copolymers prepared by the typical polymerization procedures described in Example IX and Example X, respectively, are listed in Table 1. Polymer structures were confirmed by nuclear magnetic resonance (NMR) spectroscopy. Glass transition temperatures were determined by differential scanning calorimetry (DSC). Average molecular weights (i.e., weight average molecular weights) and polydispersity index were determined by light scattering gel permeation chromatography (GPC).

TABLE 1

Polymer Properties

| Monomer(s) (Ex. No.) | Solvent | Polymerization Agent (mole % based on moles of monomer) | Reaction Temp (° C.)/Time (days) | Glass Transition Temperature (Tg) (° C.) | Polydispersity Index (PDI) | Wt. Average MW (Daltons) |
|---|---|---|---|---|---|---|
| I | CH$_2$Cl$_2$ | BF$_3$ etherate (4%) | 40/0.5 | 44 | ND | ND |
| I | CH$_2$Cl$_2$ | SbCl$_5$ (3%) | −78 to RT/0.8 | 34.1 | ND | ND |
| II | CH$_2$Cl$_2$ | BF$_3$ etherate (1%) | −100/0.8 | 32 | 1.32 | 1462 |
| I | CH$_2$Cl$_2$ | BF$_3$ etherate (1%) | −40/3 | 16.9 | ND | ND |
| V | CH$_2$Cl$_2$ | BF$_3$ etherate (1%) | −40 to RT/0.5 | 32.3 | ND | ND |
| VI | CH$_2$Cl$_2$ | BF$_3$ etherate (1%) | 0 to RT/3 | 40.6 | ND | ND |
| I | CH$_2$Cl$_2$ | ZnCl$_2$ (1%) | 0 to RT/2 | −2.3 | 1.27 | 9315 |
| I | THF | ZnI$_2$ (1%) | RT/2 | 21.7 | 1.45 | 13350 |
| I | THF | Zn(O$_3$SCF$_3$)$_2$ (1%) | RT/2 | 6 | 1.69 | 14840 |
| V | THF | ZnI$_2$(1%) | RT to 100/2 | 33.1 | ND | ND |
| I | CH$_2$Cl$_2$ | Zn(O$_3$SCF$_3$)$_2$ (1%) | RT/2 | 23.4 | 1.61 | 13280 |
| I | CH$_2$Cl$_2$ | Zn(O$_3$SCF$_3$)$_2$ (0.5%) | RT/3 | 29.5 | 1.37 | 9902 |
| I and II[†] | CH$_2$Cl$_2$ | Zn(O$_3$SCF$_3$)$_2$ (0.25%) | RT/3 | 39 | 1.56 | 3180 |
| 1 | None | Zn(O$_3$SCF$_3$)$_2$ (0.2%) | RT/3 | 25.6 | 1.45 | 4407 |
| I | None | (CH$_3$)$_3$SiOS(O)$_2$CF$_3$ (0.003%) | RT to 110/0.5 | ND | 1.53 | 896 |
| I and II[††] | toluene | Zn(O$_3$SCF$_3$)$_2$ (0.25%) | RT/3 | −0.5 | 1.68 | 1965 |
| I and II[†††] | toluene | Zn(O$_3$SCF$_3$)$_2$ (0.25%) | RT/3 | 27.6 | 1.61 | 10650 |
| I and II[††††] | toluene | Zn(O$_3$SCF$_3$)$_2$ (0.25%) | RT/3 | 25 | 1.51 | 3672 |
| I and II[†††††] | toluene | Zn(O$_3$SCF$_3$)$_2$ (0.25%) | RT/3 | 64.2 | 1.56 | 5710 |
| I | toluene | Zn(O$_3$SCF$_3$)$_2$ (0.3%) | RT/2 | 25.9 | 1.61 | 19640 |

RT = Room Temperature
ND = Not Determined
[†]I:II molar ratio was 1.7:1
[††]I:II molar ratio was 3:1
[†††]I:II molar ratio was 5:1
[††††]I:II molar ratio was 1:1
[†††††]I:II molar ratio was 0.2:1

Example XII

Hydrolysis Study

In a clean NMR tube, 44 mg of a homopolymer of the monomer of Example I (MW=13,350 g/mol) was dissolved in 0.75 mL THF-d8. The NMR spectrometer was set at 25° C. After 40 microliters H$_2$O and 5.7 microliters of formic acid (reference and catalyst) were added and shook well, spectra were acquired for 16 hours, at a rate of 60 minutes/spectrum. The decay of starting material and the formation of degradation products were monitored from their peak intensities. After normalized to each proton, a plot of the change of starting material and product versus time was found to be linear until the reaction was about 80% complete, which is consistent with a zero order reaction having the rate constants: $k_{formation}$=3.72E-05 (intensity/s) and $k_{decay}$=4.53E-05 (intensity/s).

Example XIII

Elution of Clonidine Base from a Polyketal Polymer

A polyketal polymer was prepared from the monomer described in Example I using the conditions listed in the last row of Table 1 (Example XI), resulting in a polyketal polymer having a Tg=25.9° C. and a weight average molecular weight of 19,640 daltons. The polymer was mixed with clonidine (7% wt/wt). The mixture was melted and then extruded to form rods, which were then cut into shorter lengths. Each of the rods was submerged in 10 mL of 6.7 mM PBS at pH 7.4. The samples were kept in an incubator kept at 37° C. The rods appeared to soften during the time period of testing, and ultimately transformed to spheres at the bottom of vials, or to sheets at the top of the buffer solution. The release of clonidine base was monitored by ultraviolet (UV) spectroscopy.

Figure 1:
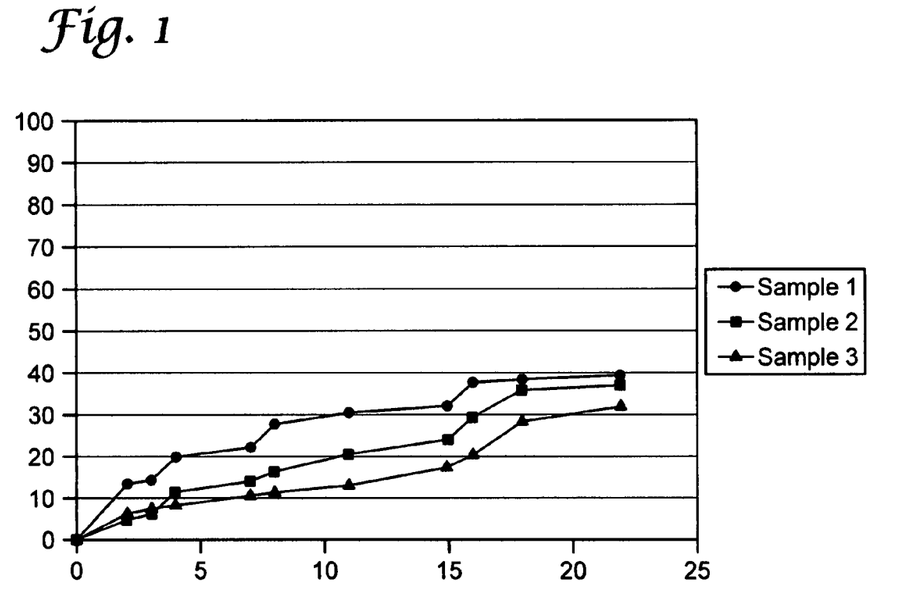
FIG. 1 is a graph of cumulative release (%; y-axis) versus time (days; x-axis) illustrating the measured cumulative release of clonidine base from a poly(ketal) polymer for three sample rods as described in Example XIII.
Figure 2:
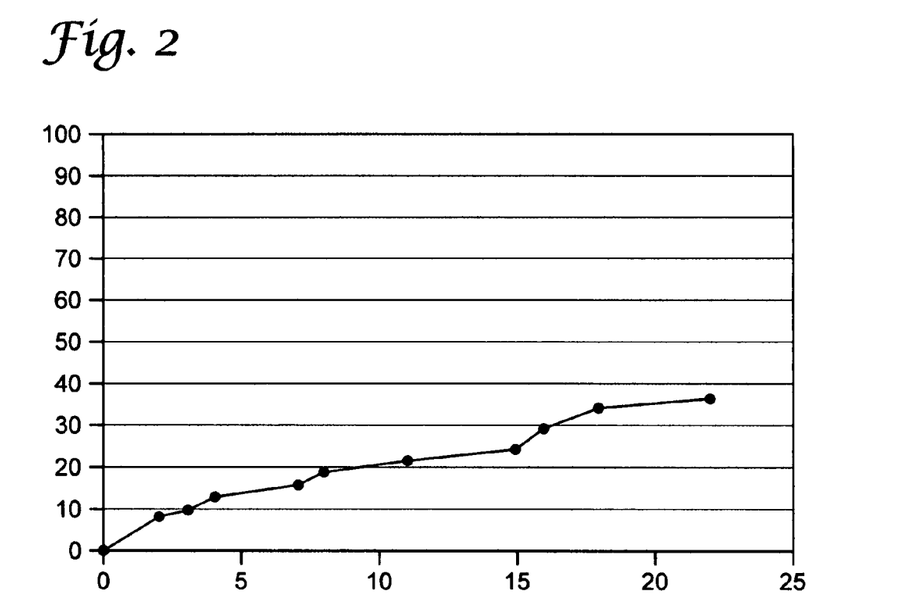
FIG. 2 is a graph of cumulative release (%; y-axis) versus time (days; x-axis) illustrating the average cumulative release of clonidine base from a poly(ketal) polymer for three sample rods as described in Example XIII.

FIG. 1 is a graph of cumulative release (%; y-axis) versus time (days; x-axis) illustrating the measured cumulative release of clonidine base from the poly(ketal) polymer for three sample rods. FIG. 2 is a graph of cumulative release (%; y-axis) versus time (days; x-axis) illustrating the average cumulative release of clonidine base from the poly(ketal) polymer for the three sample rods.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A polymer comprising two or more repeat units selected from the group consisting of:

a repeat unit of the formula (Formula III):

a repeat unit of the formula (Formula IV):

combinations thereof;

wherein:

each X independently represents NR$^5$, CR$^5$R$^6$, SiR$^5$R$^6$, S, a sulfur-bonded group, a phosphorus-bonded group, or each Y independently represents O, NR$^5$, CR$^5$R$^6$, SiR$^5$R$^6$, S, a sulfur-bonded group, a phosphorus-bonded group, or each n is independently from 0 to 5;

each R$^1$ independently represents an organic group;

each R$^2$, R$^3$, R$^4$, R$^5$, and R$^6$ independently represents H or an organic group; and R$^1$, R$^2$, R$^3$, R$^4$, R$^5$, and/or R$^6$ can optionally be joined to each other to form one or more rings.

2. The polymer of claim 1 wherein:

each X and Y independently represents CR$^5$R$^6$;

each n is 1;

each R$^1$ independently represents a C1-C10 organic group;

each R$^2$, R$^3$, R$^4$, R$^5$, and R$^6$ independently represents H or a C1-C10 organic group; and R$^1$ and R$^5$ can optionally be joined to each other to form a ring.

3. The polymer of claim 2 wherein:

each X and Y independently represents CR$^5$R$^6$;

each n is 1;

each R$^1$ independently represents a phenyl group or a C1-C4 aliphatic or alicyclic group;

each R$^2$, R$^3$, R$^4$, R$^5$, and R$^6$ independently represents H, a phenyl group, or a C1-C4 aliphatic or alicyclic group; and R$^1$ and R$^5$ can optionally be joined to each other to form a five- or six-membered ring.

4. The polymer of claim 3 wherein R$^1$=methyl; X=Y=CH$_2$; n=1; and R$^2$=R$^3$=R$^4$=H.

5. The polymer of claim 3 wherein R$^1$=phenyl; X=Y=CH$_2$; n=1; and R$^2$=R$^3$=R$^4$=H.

6. The polymer of claim 1 wherein the polymer further comprises repeat units selected from the group consisting of crosslinkable repeat units, crosslinked repeat units, repeat units having imagable groups, repeat units having latent reactive sites, and combinations thereof.

7. The polymer of claim 1 wherein the polymer further comprises repeat units selected from the group consisting of alpha-hydroxy alkanoates, beta-hydroxy alkanoates, gamma-hydroxy alkanoates, delta-hydroxy alkanoates, epsilon-hydroxy alkanoates, gylcols, carbonates, acetals, and combinations thereof.

8. The polymer of claim 1 wherein the polymer is a copolymer.

9. The polymer of claim 8 wherein the copolymer is selected from the group consisting of random copolymers, alternating copolymers, block copolymers, graft copolymers, and combinations thereof.

10. The polymer of claim 9 wherein the copolymer is a block copolymer, and at least one block of the block copolymer is a polyketal block comprising the two or more repeat units selected from the group consisting of repeat units of Formula III, repeat units of Formula IV, and combinations thereof.

11. The polymer of claim 10 wherein at least one other block of the block copolymer is a poly(lactone) block comprising repeat units selected from the group consisting of alpha-hydroxy alkanoates, beta-hydroxy alkanoates, gamma-hydroxy alkanoates, delta-hydroxy alkanoates, epsilon-hydroxy alkanoates, carbonates, acetals, and combinations thereof.

12. The polymer of claim 10 wherein at least one other block of the block copolymer is a poly(orthoester) block.

13. The polymer of claim 10 wherein at least one other block of the block copolymer is a poly(alkyleneglycol) block comprising alkylene glycol repeat units.

14. The polymer of claim 1 wherein the polymer is biodegradable.

15. The polymer of claim 1 wherein the polymer is a tissue bulking agent, a tissue replacement agent, a tissue repair agent, a surgical void filler, an agent used to prevent surgical adhesions, or a combination thereof.

16. A method of preparing a polymer according to claim 1, the method comprising:
combining components comprising a polymerization agent and at least one cyclic oxygen-containing compound under conditions effective to polymerize the at least one cyclic oxygen-containing compound, wherein the at least one cyclic oxygen-containing compound is selected from the group consisting of:
a compound of the formula (Formula I)

a compound of the formula (Formula II)

combinations thereof;
wherein:
each X independently represents $NR^5$, $CR^5R^6$, $SiR^5R^6$, S, a sulfur-bonded group, a phosphorus-bonded group, or each Y independently represents O, $NR^5$, $CR^5R^6$, $SiR^5R^6$, S, a sulfur-bonded group, a phosphorus-bonded group, or each n is independently from 0 to 5;
each $R^1$ independently represents an organic group;
each $R^2$, $R^3$, $R^4$, $R^5$, and $R^6$ independently represents H or an organic group; and
$R^1$, $R^2$, $R^3$, $R^4$, $R^5$, and/or $R^6$ can optionally be joined to each other to form one or more rings.

17. The method of claim 16 wherein:
each X and Y independently represents $CR^5R^6$;
each n is 1;
each $R^1$ independently represents a C1-C10 organic group;
each $R^2$, $R^3$, $R^4$, $R^5$, and $R^6$ independently represents H or a C1-C10 organic group; and
$R^1$ and $R^5$ can optionally be joined to each other to form a ring.

18. The method of claim 17 wherein:
each X and Y independently represents $CR^5R^6$;
each n is 1;
each $R^1$ independently represents a phenyl group or a C1-C4 aliphatic or alicyclic group;
each $R^2$, $R^3$, $R^4$, $R^5$, and $R^6$ independently represents H, a phenyl group, or a C1-C4 aliphatic or alicyclic group; and
$R^1$ and $R^5$ can optionally be joined to each other to form a five- or six-membered ring.

19. The method of claim 18 wherein $R^1$=methyl; X=Y=$CH_2$; n=1; and $R^2$=$R^3$=$R^4$=H.

20. The method of claim 18 wherein $R^1$=phenyl; X=Y=$CH_2$; n=1; and $R^2$=$R^3$=$R^4$=H.

21. A method of preparing a biodegradable medical device, the method comprising:
providing a medical device; and
applying one or more polymers according to claim 1 to at least a portion of the device.

22. A method for delivering a biologically active agent to a tissue, the method comprising:
providing a medical device comprising one or more polymers according to claim 1 and a biologically active agent disposed in at least one of the one or more polymers;
positioning the at least one polymer of the device proximate a tissue; and
allowing the at least one polymer to biodegrade and deliver the biologically active agent disposed therein.

23. A composition comprising one or more polymers according to claim 1.

24. The composition of claim 23 wherein the composition is a pharmaceutical composition further comprising a biologically active agent.

25. The composition of claim 23 further comprising an additional component selected from the group consisting of fillers, dyes, pigments, inhibitors, accelerators, viscosity modifiers, wetting agents, buffering agents, stabilizers, biologically active agents, polymeric materials, excipients, and combinations thereof.

26. A method of forming a biodegradable medical device, the method comprising shaping one or more polymers according to claim 1 to form the device.

27. A medical device comprising one or more polymers according to claim 1.

28. The medical device of claim 27 further comprising a biologically active agent.

29. The medical device of claim 28 wherein the biologically active agent is disposed in at least one of the one or more polymers.

30. A method of controlling the release rate of a biologically active agent from a medical device, the method comprising:

providing a medical device comprising one or more polymers according to claim 1; and disposing a biologically active agent in at least one of the one or more polymers to control the release rate of the biologically active agent from the medical device.

31. A method of repairing or replacing tissue, the method comprising disposing one or more polymers according to claim 1 proximate a tissue in need of repair or replacement.

* * * * *